(12) United States Patent
Burkhardt et al.

(10) Patent No.: US 6,201,391 B1
(45) Date of Patent: Mar. 13, 2001

(54) NONLINEAR HARMONICS METHOD AND SYSTEM FOR MEASURING DEGRADATION IN PROTECTIVE COATINGS

(75) Inventors: Gary L. Burkhardt, Adkins; Hegeon Kwun, San Antonio, both of TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 09/168,185

(22) Filed: Oct. 7, 1998

(51) Int. Cl.⁷ .......................... G01B 7/06; G01B 121/02; G01R 33/12
(52) U.S. Cl. ............................................. 324/233
(58) Field of Search .................... 324/229, 230, 324/231, 236, 239, 260, 209

(56) References Cited

U.S. PATENT DOCUMENTS

| | | | |
|---|---|---|---|
| 3,636,437 | 1/1972 | Soulant, Jr. et al. | 73/779 |
| 3,783,370 | 1/1974 | Birdwell et al. | 324/209 |
| 3,792,348 | 2/1974 | Rollwitz et al. | |
| 4,799,011 | 1/1989 | Muller | 324/233 |
| 4,843,320 | 6/1989 | Spies | 324/240 |
| 4,881,031 | 11/1989 | Pfisterer et al. | 324/233 |
| 5,047,717 | 9/1991 | Hofer | 73/779 |
| 5,180,969 | 1/1993 | Kwun | 324/240 |
| 5,313,405 | 5/1994 | Jiles et al. | 324/209 |
| 5,400,656 | 3/1995 | Schiessle et al. | 73/779 |
| 5,532,589 | 7/1996 | Gammell | 324/228 |
| 5,565,773 | 10/1996 | Inaguma et al. | 324/239 |
| 5,619,135 | 4/1997 | Kohn et al. | 324/239 |
| 5,640,088 | 6/1997 | Sasahara et al. | 324/209 |
| 5,698,977 | 12/1997 | Simpson et al. | 324/209 |

*Primary Examiner*—Jay Patidar
(74) *Attorney, Agent, or Firm*—Taylor Russell & Russell, P.C.

(57) ABSTRACT

A system and method for nondestructive testing of a workpiece having a metallic protective coating utilizing nonlinear harmonics techniques to determine degradation within the metallic protective coating. The invention use a time-varying magnetic field to sense magnetic properties of the protective coating. The odd-numbered harmonic frequencies are detected and their amplitudes are related to the magnetic condition of the material under test to determine coating degradation. When no harmonic signal caused by an induced magnetic field is detected, the coating is not degraded. When a harmonic signal is detected, the coating has degraded. Nonlinear harmonics techniques are used to determine the amount of coating degradation.

31 Claims, 11 Drawing Sheets

NONLINEAR HARMONICS METHOD AND SYSTEM FOR MEASURING DEGRADATION IN PROTECTIVE COATINGS

BACKGROUND

The invention relates generally to nondestructive methods for measuring service-related degradation in protective coatings such as those used to protect gas turbine blades from high temperature oxidation and corrosion. More particularly, the invention is a method and system that uses nonlinear harmonic detection methods to sense degradation-related changes in the magnetic permeability of the high-temperature protective coatings applied to the surface of a workpiece. The invention uses a time-varying magnetic field at a fundamental frequency to detect changes in the magnetic properties of the coatings. The odd-numbered harmonic frequencies are detected and their amplitudes are related to the magnetic permeability of the coating under test to determine coating degradation. By using different fundamental frequencies, it is possible to profile coating degradation with depth and minimize coating thickness effects.

Metallic coatings are commonly used on metal components to protect the surfaces of the components from high-temperature oxidation and corrosion. A common use is on combustion turbines to protect the surfaces of components such as blades. One such class of metallic coatings used for protection typically has the composition MCrAlY, where M may represent either cobalt (Co), nickel (Ni), or a combination of both, Cr represents chromium, Al represents aluminum and Y represents yttrium. Detection of degradation or failure of the metallic coatings is important to prevent damage to the underlying components. During service, the aluminum (AL) in the coating diffuses inward into the base material of the component and outward to form a protective aluminum oxide layer which forms on the outside surface of the coating. Eventually, the aluminum in the coating becomes depleted and can no longer support the aluminum oxide layer. This results in coating failure and lack of protection for the underlying component, such as the blade base metal of combustion turbine components. Coatings can be stripped and replaced, provided this is done before the coating fails. If the protective coating has degraded to the point where it is no longer functional, damage to the underlying component can occur primarily due to high temperature oxidation or corrosion of the material. If the degradation of the coating is not detected prior to coating failure, it may be necessary to replace the entire component.

It has been observed that in some classes of coating systems, degradation causes the coating to change from an initial nonferromagnetic condition to a ferromagnetic condition. By measuring the magnetic properties of the coating, it is possible to nondestructively determine the condition of the coating. Techniques using eddy currents and permeability probes have been applied to this problem. The eddy current measurement technique uses a time-varying magnetic field to induce eddy currents into the component. The eddy current sensing device always generates a reading even if the material is in a nonferromagnetic state (and therefore the coating is not degraded) because the component material is electrically conductive and the eddy current method responds to conductivity as well as magnetic condition. Also, if the thickness of the coating changes, the eddy current measurement will change even if the coating is not degraded. As the coating degrades, the eddy current reading changes only slightly and it is difficult to determine that this small change is due to degradation and not to other factors.

The permeability probe uses a permanent magnet which supplies a non-time-varying magnetic field and a magnetic sensor, such as a Hall-effect probe, to sense the magnetic field. The presence of ferromagnetic material, such degraded coating, affects the field distribution and the field measured by the magnetic sensor. Both the eddy current and permeability probe measurements are sensitive to the magnetic condition of the coating and to probe liftoff and tilting effects. The eddy current measurements are also sensitive to electrical conductivity and to the thickness of the coating even when the coating is not degraded. Even though the permeability probe is sensitive to coating thickness after the coating has degraded, because a permanent magnet is used, it is not possible to use different frequencies to control penetration into the coating (skin depth) so as to be able to vary penetration depth into the coating, nor is it possible to profile coating degradation with depth. These variations in measurement capability and sensitivity make it difficult to accurately detect and characterize coating degradation.

Therefore, a nondestructive evaluation technique is needed which can be used in the field to provide an accurate measurement of coating degradation so that the coating may be replaced before damage to the underlying component occurs. There is also a need for a technique that is not sensitive to probe liftoff and tilting effects, electrical conductivity and thickness of the coating. In addition, a technique is needed that allows a profile of coating degradation as a function of depth.

SUMMARY

The present invention is a nondestructive system and method for measuring service-related degradation in protective coatings, usually high temperature protective coatings such as those used to protect gas turbine blades from high temperature oxidation and corrosion. The invention uses nonlinear harmonics detection methods to sense degradation-related changes in the magnetic permeability of the coating applied to a component. When the coating is first applied to a component, the coating is initially nonferromagnetic. Degradation causes the coating to change from an initial nonferromagnetic condition to a ferromagnetic condition. The nonlinear harmonics method detects this change in the ferromagnetic properties of the coating of the component.

The nonlinear harmonics method is typically implemented by applying a sinusoidal current at a fundamental excitation frequency to the component of interest using an excitation coil. Any resulting magnetic induction is measured with a magnetic field sensor such as a sensing coil. The excitation frequency can range between about 1 kHz to about 10 MHz. The sensor output is amplified and the harmonic frequency content, typically the third harmonic, is determined using a spectrum analyzer or lock-in amplifier referenced to the driving waveform. Simpler configurations such as band-pass filtering the third harmonic frequency and detecting the output may also be used.

When the coating applied to the material is not degraded, the coating is nonferromagnetic so no magnetic signal is induced using the nonlinear harmonics method. Since there is no signal, there are no odd-numbered harmonic frequencies generated. As the coating on the component degrades, it becomes ferromagnetic. Because of magnetic hysteresis and nonlinear permeability of ferromagnetic material, the magnetic induction in the material becomes distorted. The distorted magnetic induction waveform contains odd numbered harmonic frequencies of the applied magnetic field.

The distorted magnetic induction waveform contains odd harmonic frequencies of the applied magnetic field. Using this nonlinear harmonics method, one or more of these harmonic frequencies are detected and their amplitudes are related to the magnetic properties of the material under test. Coating degradation may then be identified and characterized by the nonlinear harmonics response. Probe liftoff and probe tilt effects can be minimized by utilizing phase information in the signal and by combining measurements of both the fundamental frequency and the harmonic frequency or by using multiple harmonic frequencies. In addition, by adjusting the fundamental frequency, the penetration depth of the magnetic field into the coating can be controlled thus allowing profiling of the coating with depth. By using high excitation frequencies, the penetration depth may be limited to the near surface of the coating and coating thickness effects are minimized.

The present invention comprises a system for nondestructive testing utilizing nonlinear harmonics techniques to determine degradation within metallic protective coatings affixed to a surface of a workpiece. The invention has a means for supplying a time varying current at a fundamental frequency to a nonlinear harmonic sensor and for outputting a phase reference signal. The nonlinear harmonic sensor comprises an excitation coil for generating a magnetic field when supplied with the time varying current and a sensing coil for detecting a signal caused by an induced magnetic field in the metallic coating. Both the excitation and sensing coils are positioned in close proximity to the surface of the workpiece having a metallic coating. The present invention also comprises a means for amplifying and selecting a portion of the detected signal that represents the harmonic frequency component of the signal and generating an output signal using the phase reference signal, along with a means for displaying the output signal. The means for supplying the time varying current at the fundamental frequency to a nonlinear harmonic sensor and for outputting the phase reference signal may be a signal generator and power amplifier. The means for displaying the output signal may be a computer controlled display device or a meter that displays a harmonic amplitude of the output signal. In an alternate embodiment, a computer means may be used for displaying and analyzing the harmonic signal to detect coating degradation.

When no harmonic signal caused by an induced magnetic field in the metallic coating is detected, the metallic protective coating is not degraded. When a harmonic signal caused by an induced magnetic field in the metallic coating is detected, the metallic protective coating is degraded. The metallic coating may be a high temperature protective coating and may contain elements selected from the group consisting of cobalt, nickel, chromium, yttrium and aluminum.

The harmonic signal may be typically at a third harmonic frequency of the fundamental frequency. The harmonic signal stored for analysis comprises in-phase and quadrature signal components. The phase reference signal component is output to an amplifier which generates and in-phase and quadrature reference signal component. The fundamental frequency may be a selected frequency in the range of between about 1 kHz to about 10 MHz.

The means for amplifying and selecting the portion of the signal that represents the harmonic frequency component of the signal and generating a harmonic signal using the phase reference signal may further comprise a filter means for filtering the output signal to remove frequencies other than harmonic frequencies. It may also comprise a means for frequency multiplying the phase reference signal and passing the multiplied phase reference signal to a lock-in amplifier that uses the multiplied phase reference signal and filtered harmonic signal to generate a complex harmonic signal with in-phase and quadrature signal components.

The invention also comprises a method for nondestructive testing utilizing nonlinear harmonics techniques to determine degradation within metallic protective coatings affixed to a workpiece comprising the steps of: supplying a time varying current at a fundamental frequency to an excitation coil, positioned in close proximity to a surface of a workpiece having a metallic coating, for generating a magnetic field and outputting a fundamental phase reference signal, and detecting a signal caused by an induced magnetic field using a sensing coil positioned in close proximity to the surface of the workpiece. The portion of the signal that represents a harmonic frequency component of the signal is amplified and output. Both the harmonic signal and phase reference signals are stored and the amplitude of the harmonic signal is analyzed to detect coating degradation using a computer program. The method may further comprise analyzing the amplitude of the in-phase and quadrature harmonic signal components which contain coating degradation components and probe liftoff signal components and determining the amount to phase shift the in-phase and quadrature harmonic signal components to remove the liftoff signal components. The in-phase and quadrature signal components are phase shifted by a selected number of degrees to remove the liftoff signal components, with the resulting signal indicating the coating degradation components. The number of degrees of phase shifting may be determined by using an optimization software program which phase shifts the signal in incremental amounts to determine a largest amplitude for a signal of interest and a smallest amplitude for a signal not of interest.

Analyzing the amplitude of the harmonic signal to detect coating degradation may further comprise comparing the amplitude of the in-phase and quadrature harmonic signal components to an amplitude of a threshold signal level and characterizing the amount of coating degradation using a calibration curve, if the amplitude of the in-phase and/or quadrature harmonic signal is greater than the amplitude of a threshold level. The threshold level signal may be determined by using a specimen that is the same material as the workpiece having the same coating on the surface of the workpiece, placing a nonlinear harmonics sensing device on the specimen, supplying a time varying current at a given frequency to the nonlinear harmonics sensing device and outputting a fundamental phase reference signal, detecting a signal caused by induced magnetic field in the specimen, amplifying and selecting a portion of the signal of that represents a harmonic frequency component of the signal and generating a harmonic signal. The coating of the specimen may be degraded by a known amount and the steps above repeated. A calibration curve may then be constructed by plotting the harmonic signal corresponding to each degradation of the coating to generate a threshold signal level. The calibration curve can also be used to characterize coating degradation. Alternatively, the threshold level signal may be determined by using a specimen that is the same material as the workpiece with the same coating and having a known amount of coating degradation.

The fundamental frequency may be a high fundamental frequency. The high fundamental frequency may correspond to a skin penetration depth that is less than or equal to the smallest coating thickness, so a coating thickness change outside of the smallest coating thickness does not affect the harmonic frequency components. The method can be repeated for a plurality of selected high fundamental frequencies, with the selected frequencies ranging from between a frequency with a skin penetration depth that is near the surface of the coating to between a frequency with a skin penetration depth equal to or greater than the entire coating thickness. The amplitudes of the harmonic signals at the selected frequencies may then be compared to profile coating degradation as a function of depth.

BRIEF DESCRIPTION OF THE DRAWINGS

These and other features, aspects, and advantages of the present invention will become better understood with regard to the following description, appended claims, and accompanying drawings where:

DETAILED DESCRIPTION

Figure 1A:
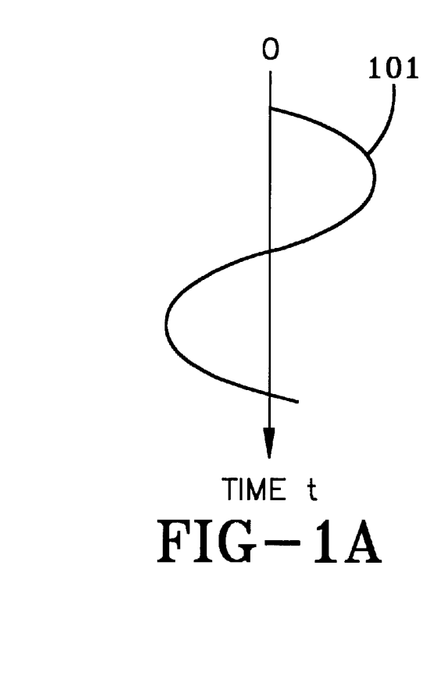
FIGS. 1A, 1B and 1C show the distortion of magnetic induction in a ferromagnetic material caused by hysteresis and nonlinearity.
Figure 1B:
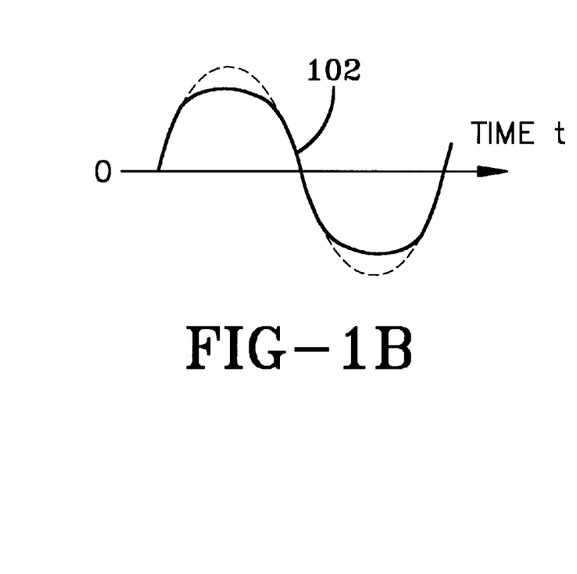
Figure 1C:
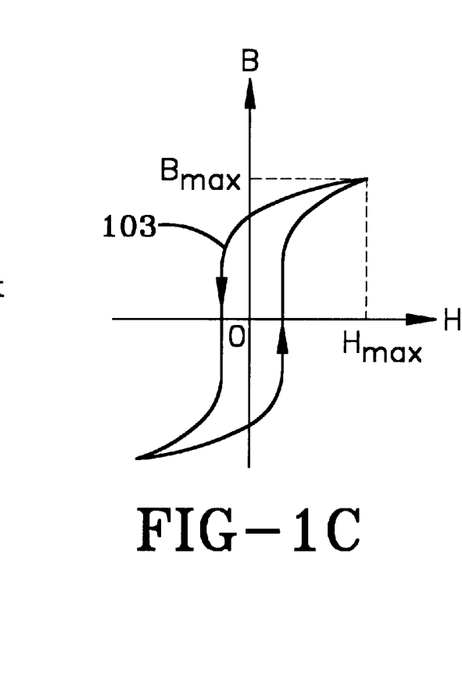

Turning now to FIGS. 1A, 1B and 1C, the distortion of magnetic induction in a ferromagnetic material caused by hysteresis and nonlinearity is shown. When a sinusoidal external magnetic field H, 102 in FIG. 1A is applied to a ferromagnetic material, the resulting magnetic induction, B 102 in FIG. 1B is not sinusoidal but distorted because of the magnetic hysteresis and nonlinear permeability of the material which is shown in FIG. 1C. This distorted waveform 102 of the magnetic induction, or equivalently the voltage induced in a coil by the magnetic induction, contains odd harmonic frequencies of the applied magnetic field. The amount of harmonic component depends on the shape of the hysteresis loop 103 (FIG. 1C).

Figure 2:
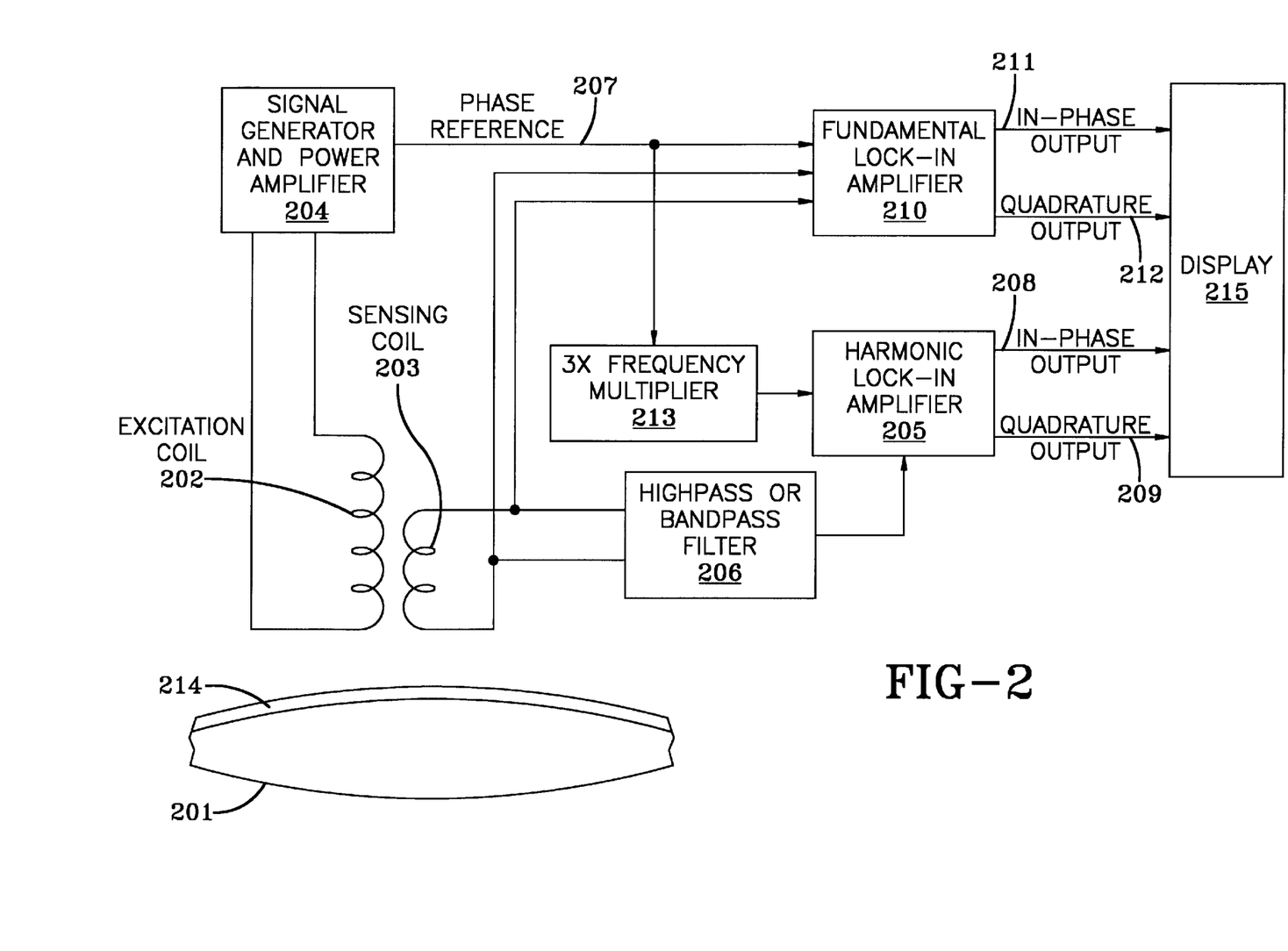
FIG. 2 shows a block diagram of a nonlinear harmonics sensing system in accordance with the present inventive concept.

The nonlinear harmonics techniques may be implemented with the arrangement shown in FIG. 2. FIG. 2 is a block diagram of a nonlinear harmonics sensing system used on a workpiece 201 having a protective coating 214. The magnetic field is applied to the coating 214 by an excitation coil 202. The resulting magnetic induction is measured with a magnetic field sensor such as a sensing coil 203. A sinusoidal current of a given frequency is supplied to the excitation coil 202 using a signal generator and power amplifier 204. If the coating 214 is not degraded it remains nonferromagnetic, so no voltage at harmonic frequencies is induced in the sensing coil 203. Therefore, there is no signal detected and there is no harmonic frequency content. When the coating 214 has degraded, it becomes ferromagnetic and voltages at harmonic frequencies are induced in the sensing coil 203, which is amplified and its harmonic frequency component, typically the third harmonic, is determined using a spectrum analyzer or harmonic lock-in amplifier 205 referenced to the driving waveform. The phase reference signal 207 is passed through a frequency multiplier 213 that multiplies the fundamental or excitation frequency (in this case by three) and passes it to the harmonic lock-in amplifier 205. The induced voltage in the sensing coil 203 is also output to the fundamental lock-in amplifier 210. A phase reference signal 207 is sent from the signal generator and power amplifier 204 to the fundamental lock-in amplifier 210. Prior to being passed to the harmonic lock-in amplifier 205, the sensor output may be passed through a high pass or bandpass filter 206 to reduce the fundamental component. Simpler configurations such as bandpass filtering the harmonic frequency and detecting the output could also be used. Two orthogonal signal outputs, an in-phase output 208 and a quadrature output 209 are output from the harmonic lock-in amplifier 205. A fundamental in-phase signal output 211 and a fundamental quadrature signal output 212 are output from the fundamental lock-in amplifier 210. The induced voltage in the sensing coil 203 contains odd numbered harmonics, with the third harmonic frequency having the highest amplitude among the harmonics. In general, the amplitude of harmonics higher than the third are quite small. Therefore, generally the amplitude of the third harmonic frequency is used to determine coating degradation and to characterize the amount of degradation, however other harmonic frequencies may also be used. The arrangement in FIG. 2, may also consist of a plurality of excitation coils and sensing coils that may be placed in different locations on the workpiece 201 to characterize coating 214 degradation at different locations along the surface of the workpiece 201. The harmonic and fundamental in-phase and quadrature signal outputs 208, 209, 211 and 212 are fed to a display device 215 which may be a meter or other type device which displays the amplitude of any signal output.

Figure 3:
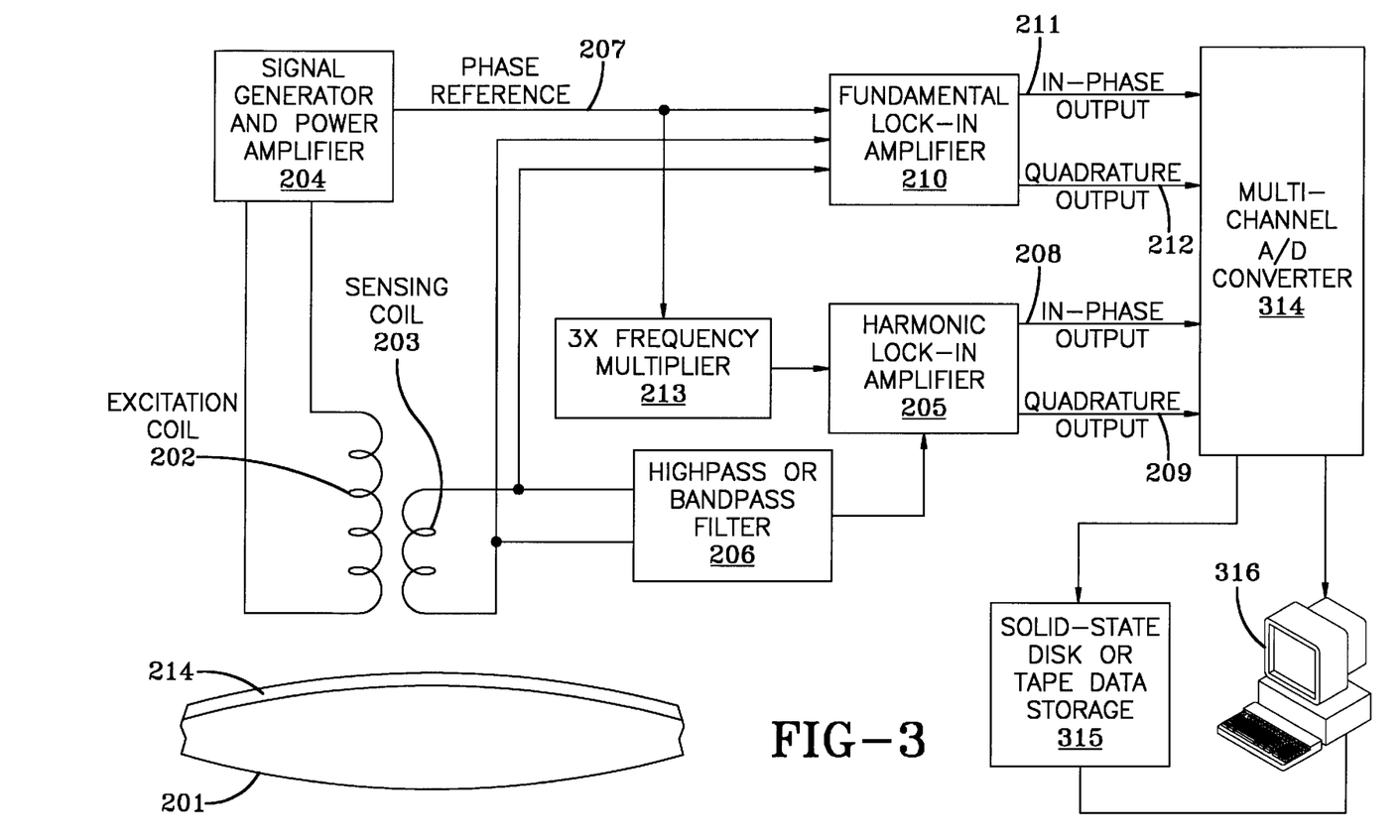
FIG. 3 shows a block diagram of an alternative embodiment of a nonlinear harmonics sensing system with the present inventive concept.

FIG. 3 shows a block diagram of an alternative embodiment of the nonlinear harmonics sensing system. FIG. 3 is similar to the embodiment shown in FIG. 2 with the exception that the harmonic and fundamental in-phase and quadrature signal outputs 208, 209, 211 and 212 are fed first to a multi-channel analog digital converter 314. After conversion, the date may be recorded on a data storage device 315, such as a solid state, disk or tape data storage device. The data may also be displayed on a computer controlled display device 316. The computer 316 may also be used for further analysis of the harmonic and fundamental signal data to detect and characterize coating degradation, display the results and store the results within the computer 316 or on a data storage device 315. and then display.

Figure 4:
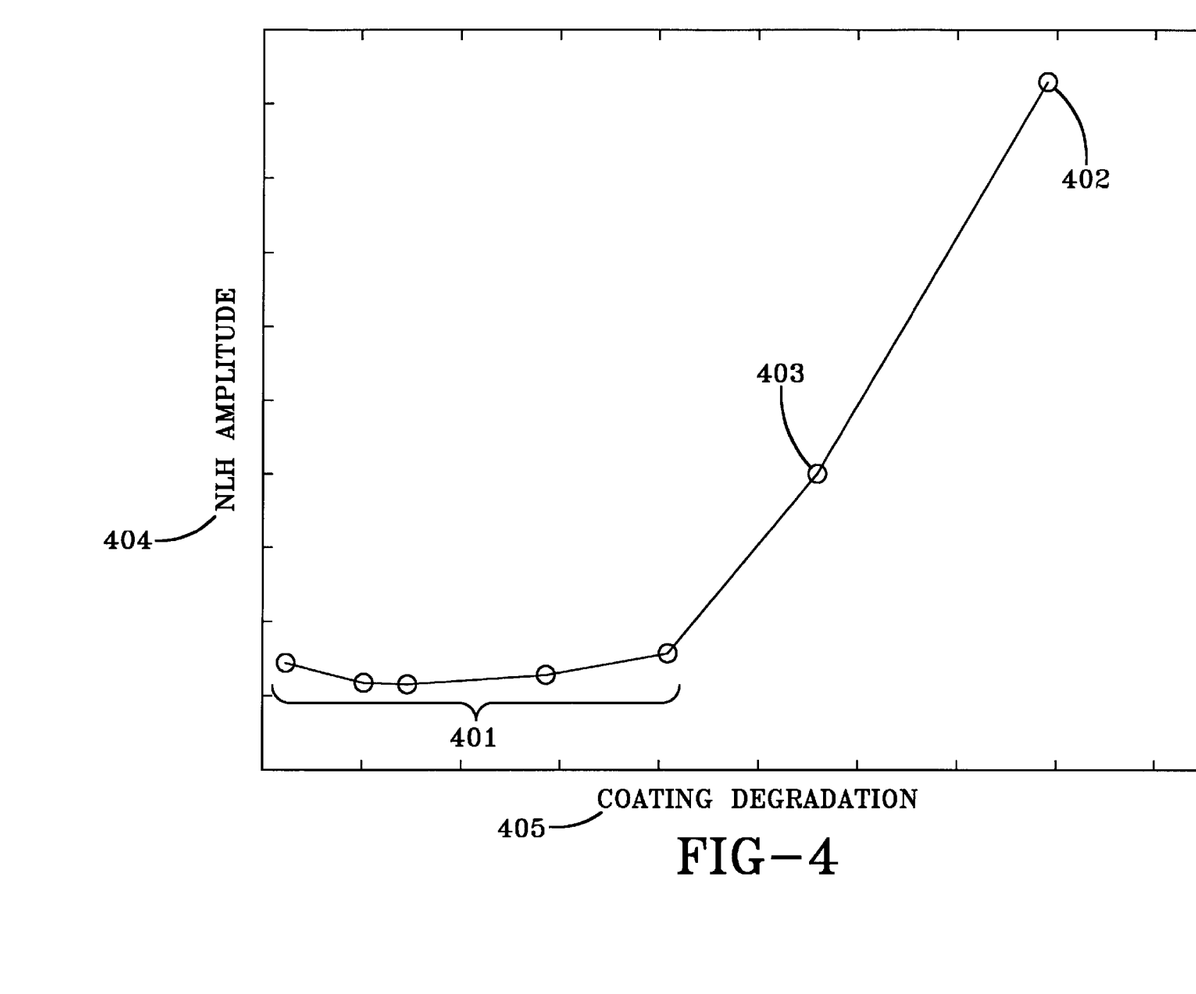
FIG. 4 shows a plot of nonlinear harmonics measurement data from a metallic coated turbine blade with coating degradation in accordance with the present inventive concept.

FIG. 4 shows a plot of nonlinear harmonics measurement data from a metallic coated turbine blade with coating degradation. The blade has a CoCrAlY coating applied. The plot of the measurements shows the magnitude of the third harmonic 404 obtained with 10 kHz excitation versus coating degradation 405. The measurements were taken at numerous locations along a line on the surface of the blade. The blade was sectioned metallurgically and its condition was found to range from little or no degradation 401 to 100-percent degradation 402. As the coating begins to degrade 403 until it is 100-percent degraded 402, the nonlinear harmonics response increased dramatically in response to the degradation.

Figure 5A:
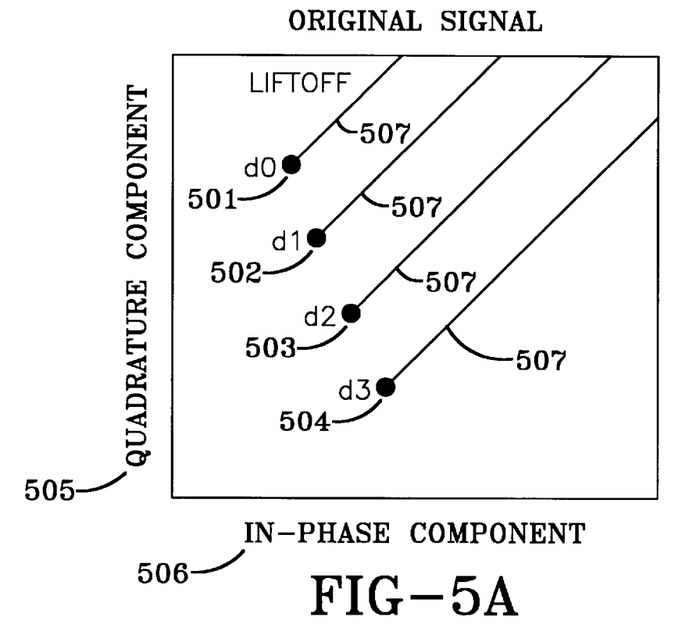
FIG. 5a shows a plot of nonlinear harmonics response to probe liftoff from a coated surface with varying amounts of coating degradation in accordance with the present inventive concept.

FIG. 5a shows a plot of nonlinear harmonics response to probe liftoff from a coated surface with varying amounts of coating degradation 501–504. The nonlinear harmonics response is shown as the quadrature component 505 plotted versus the in-phase component 506. The liftoff lines 507 on the graph are at an angle of approximately 45 degrees from either the quadrature 505 or in-phase axis 506. A changed in liftoff 507, as well as a change in coating degradation, will affect both the quadrature 505 and in-phase components 506.

Figure 5B:
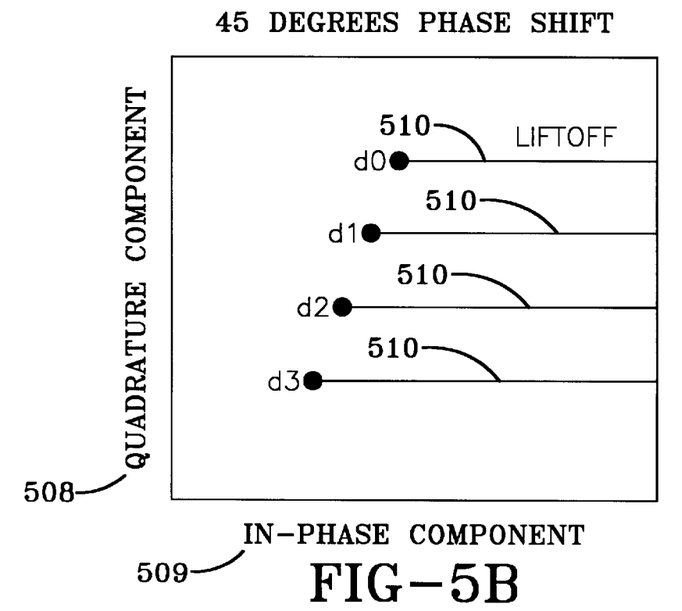
FIG. 5b shows the data from FIG. 5b after phase shifting in accordance with the present inventive concept.

FIG. 5b shows the data from FIG. 5b after phase shifting in accordance with the present inventive concept. The nonlinear harmonics response is shown as the quadrature component 508 plotted versus the in-phase component 509. In FIG. 5b, the data has been rotated by 45 degrees in the clockwise direction by shifting the phase. The liftoff lines 510 are now approximately horizontal. This means that a change in liftoff 510 will only affect the in-phase component 509. Using this rotation, the quadrature component 508 can then be monitored for changes in coating degradation, independently of liftoff 510 variations will occur primarily in the in-phase component 509.

Figure 6:
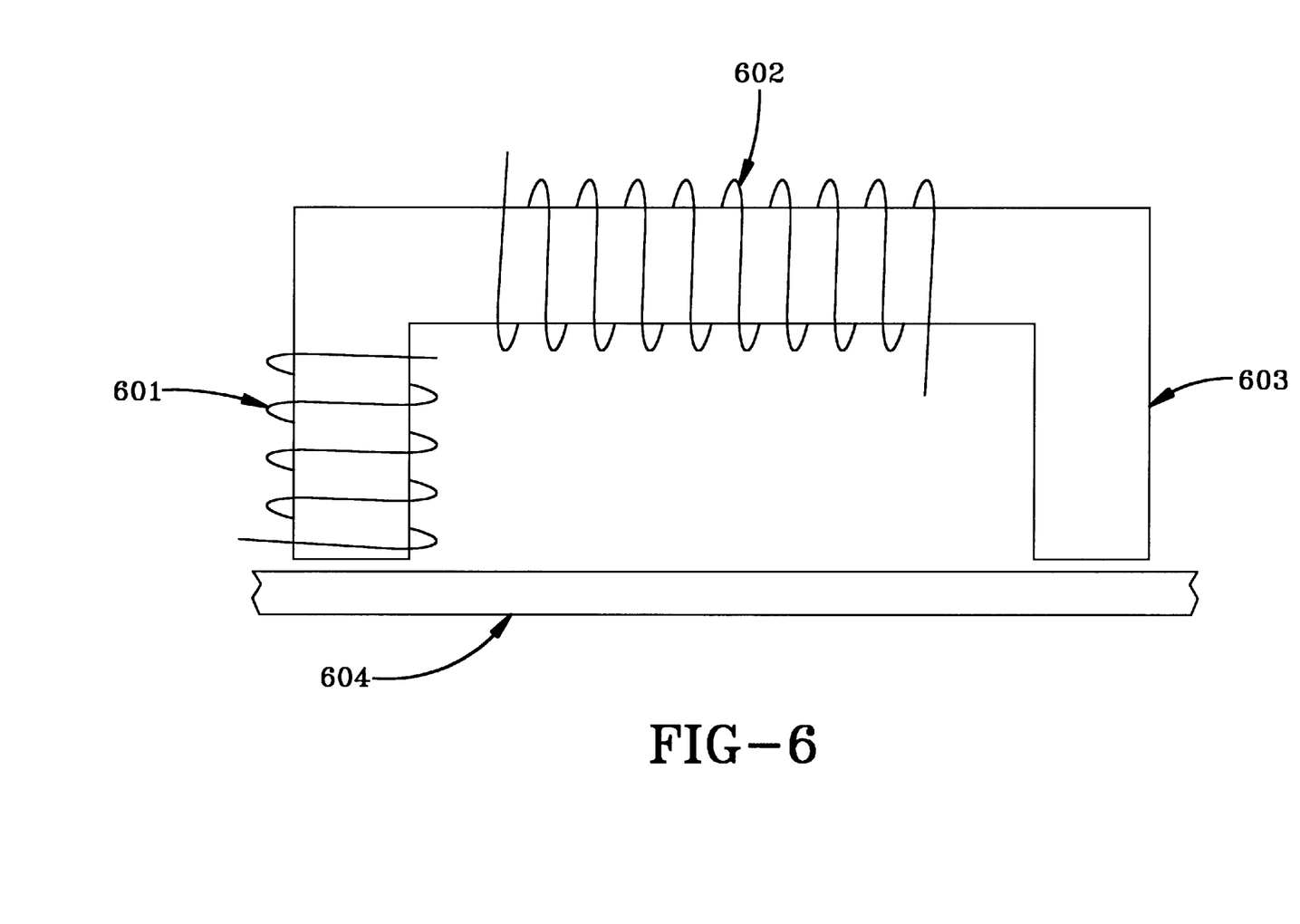
FIG. 6 shows a typical nonlinear harmonics sensor probe configuration in accordance with the present inventive concept.

FIG. 6 shows a typical nonlinear harmonics sensor probe configuration. The sensing coil 601 and excitation coil 602 are wrapped around a ferrite core 603, and are placed in close proximity to the workpiece 604.

Figure 7:
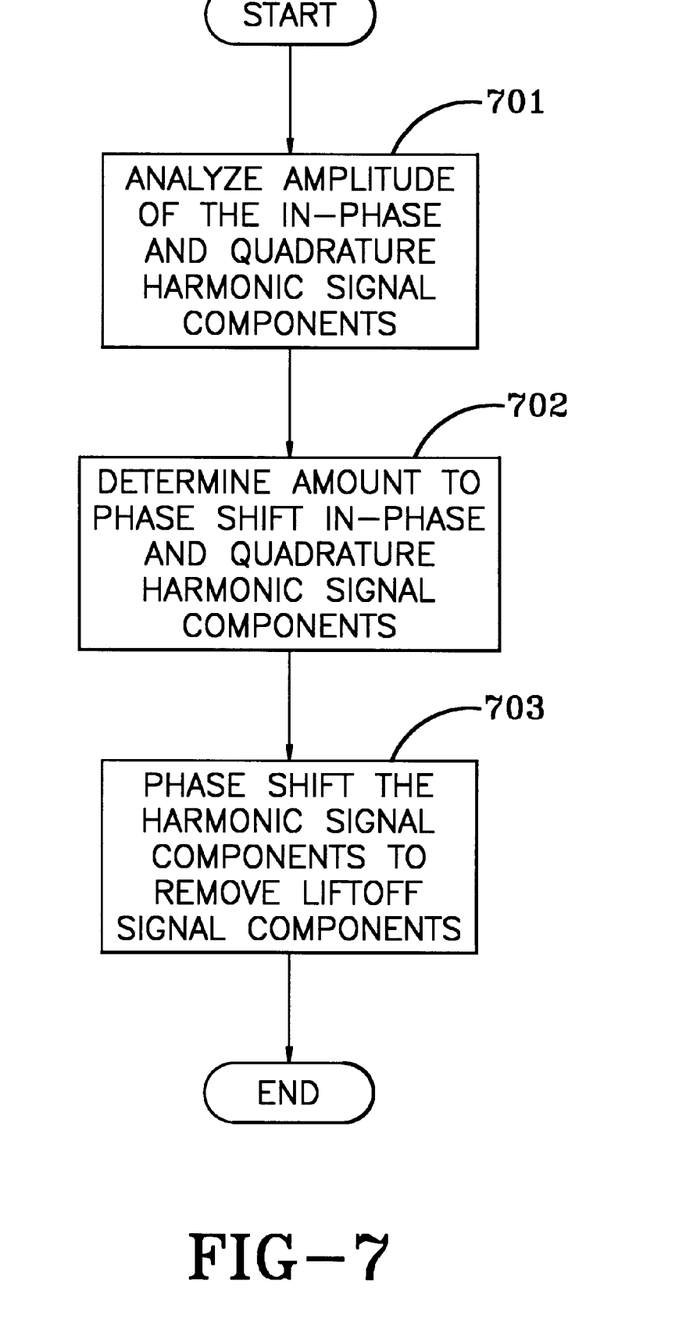
FIG. 7 is a flowchart of a method of analyzing the harmonic signal to detect coating degradation in accordance with the present inventive concept.

FIG. 7 is a flowchart of a method of analyzing the harmonic signal for coating degradation. The amplitude of the in-phase and quadrature harmonic signal components is analyzed 701. The amount to phase shift the in-phase and quadrature harmonic signal components is determined 702 and the in-phase and quadrature harmonic signal components are shifted by a selected number of degrees 703 to remove the liftoff signal components with the resulting signal indicating the areas of coating degradation. The amount to phase shift the signal is determined such that the result after phase shifting is similar to that shown in FIG. 5b, where the liftoff components are removed from the quadrature harmonic signal component.

Figure 8:
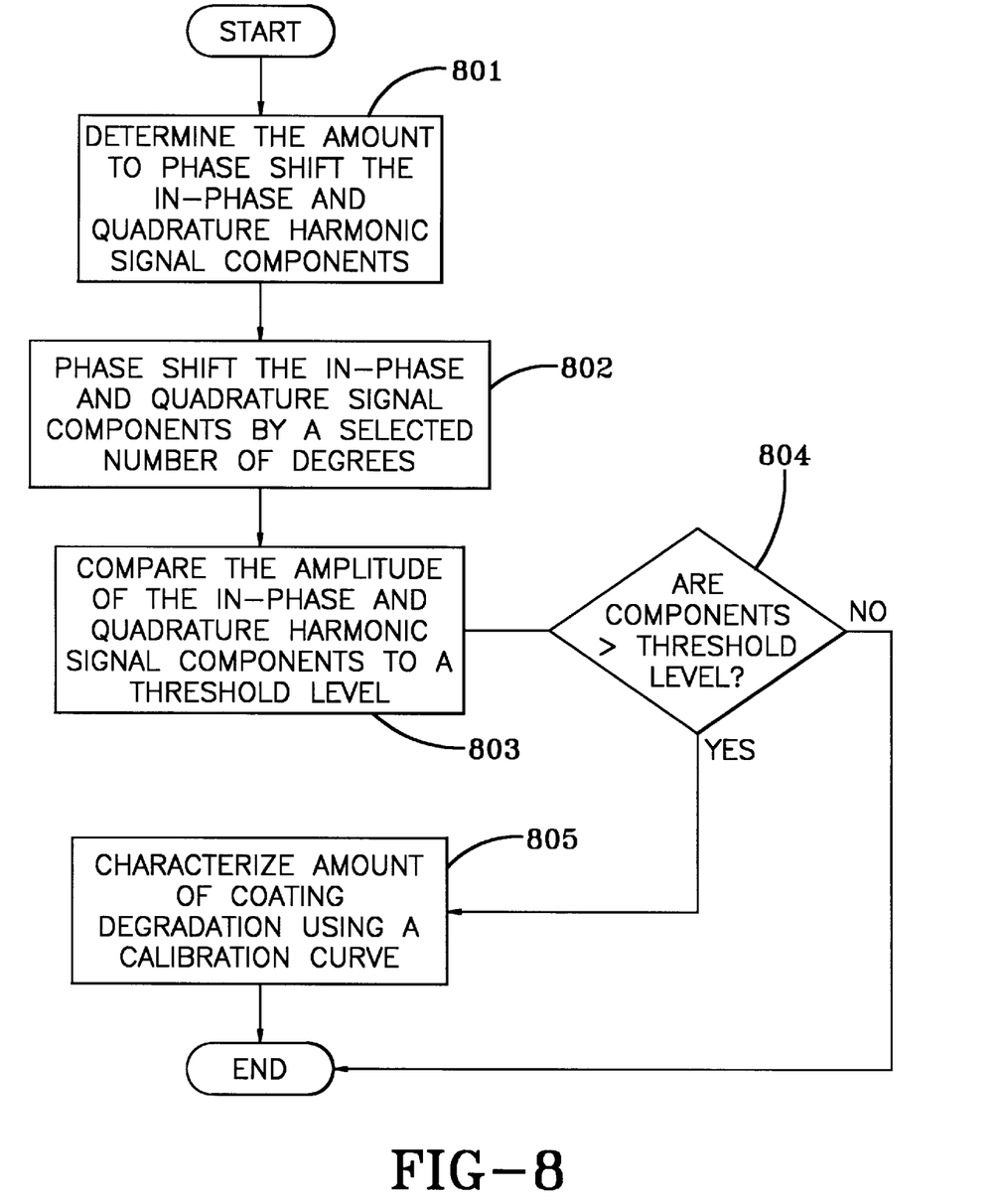
FIG. 8 is a flowchart of an alternative method of analyzing the harmonic signal to detect coating degradation in accordance with the present inventive concept.

FIG. 8 is a flowchart of an alternative method of analyzing the harmonic signal to detect coating degradation. The amount to phase shift the in-phase and quadrature harmonic signal components is determined 801. The in-phase and quadrature harmonic signal components are shifted by a selected number of degrees 802 to remove the liftoff signal components with the resulting signal indicating the areas of coating degradation. The amplitude of the in-phase and quadrature harmonic signal components is compared to a threshold level 803. If the components are greater than the threshold level 804, the amount of coating degradation is characterized using a calibration curve 805. If the components are less than the threshold level 804, the signal is not of interest and processing ends.

Figure 9:
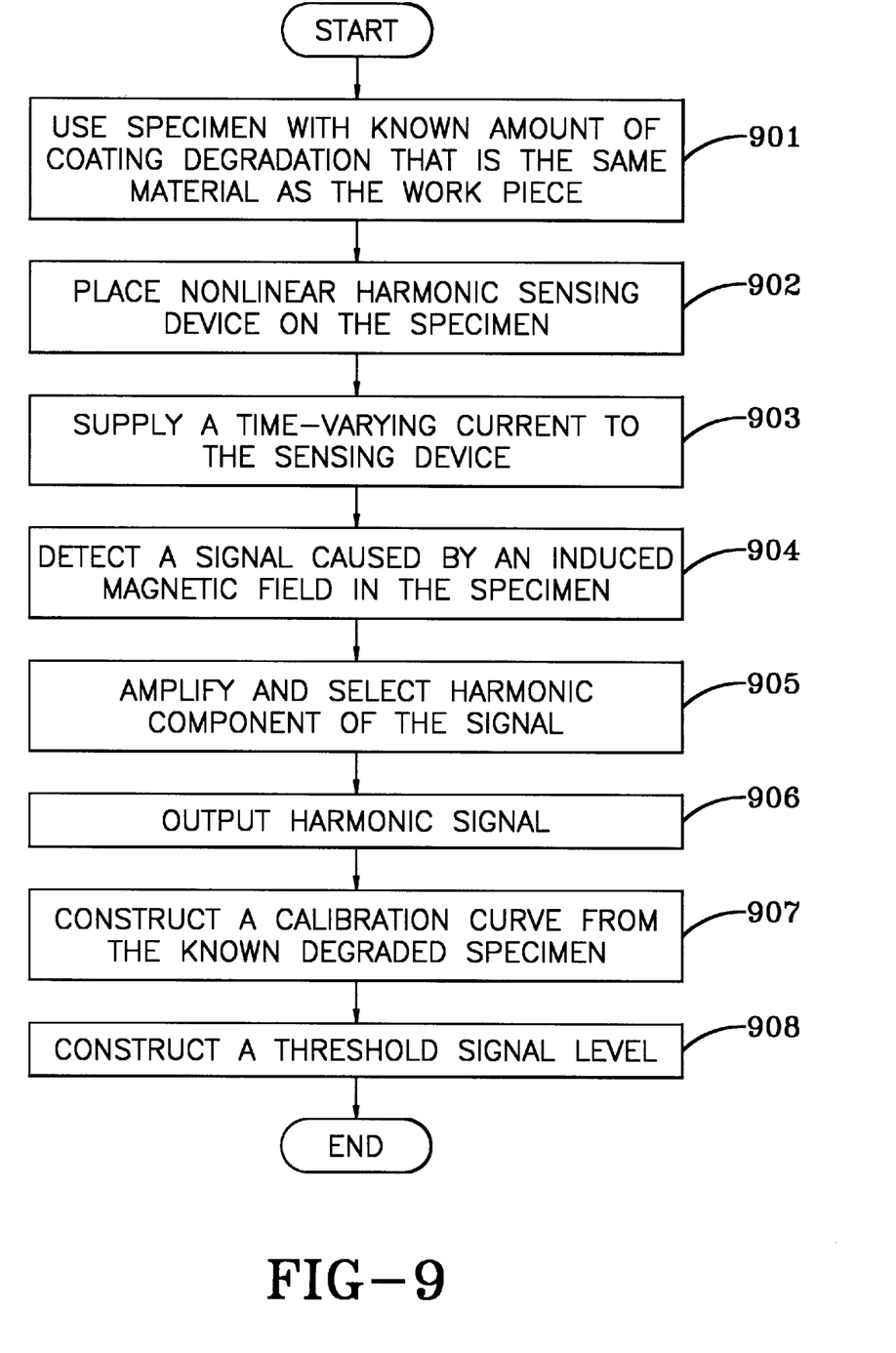
FIG. 9 is a flowchart of a method of determining the threshold level signal and constructing a calibration curve in accordance with the present inventive concept.

FIG. 9 is a flowchart of a method of determining the threshold level signal and constructing a calibration curve. Using a specimen of the same material as the workpiece with a known amount of coating degradation 901, a nonlinear harmonics sensing device is placed on the specimen 902. A time varying current is supplied to the sensing device 903. A signal caused by an induced magnetic field in the specimen is detected 904. The harmonic component of the signal is selected and amplified 905 and a harmonic signal is output 906. The process of steps 901 through 906 is then repeated for a plurality of specimens with known amounts of coating degradation. After all of the specimens have been measured, a calibration curve is constructed from the known coating degradation of the specimens 907 and a threshold signal level is constructed 908.

Figure 10:
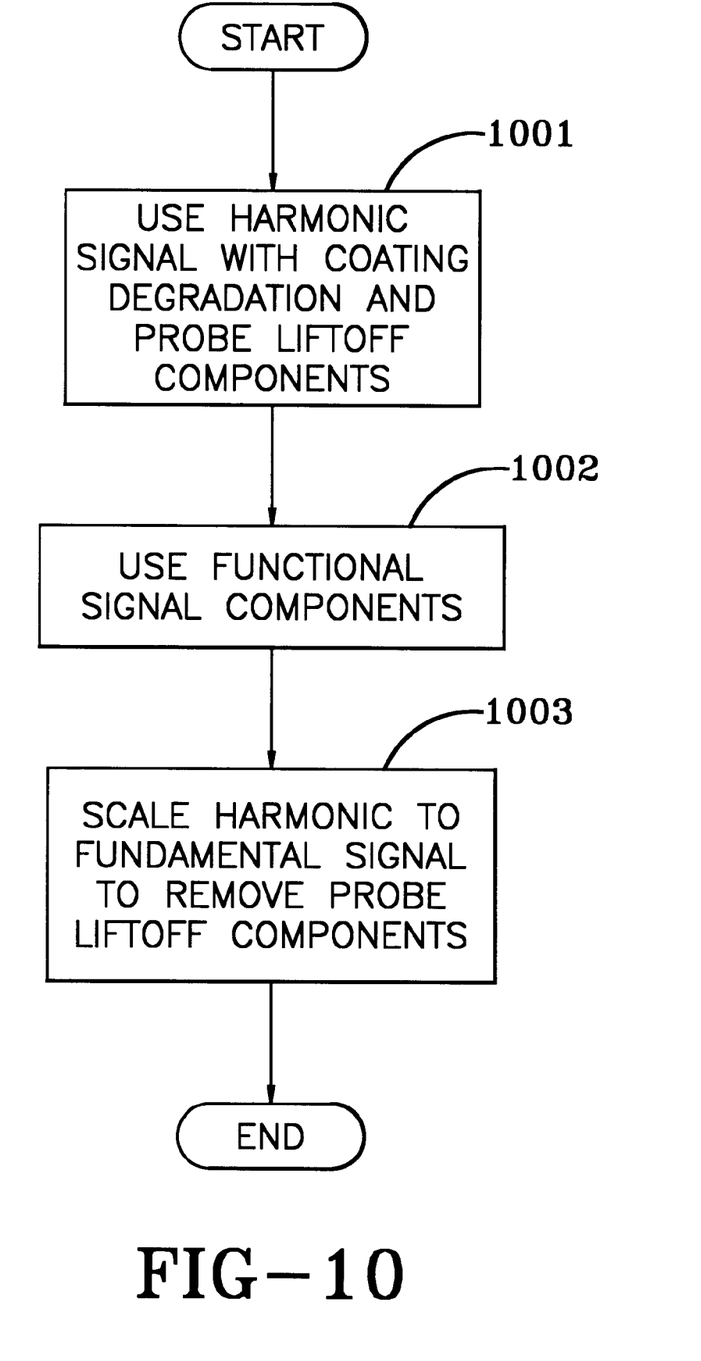
FIG. 10 is a flowchart of an alternative method of analyzing the amplitude of the harmonic signal to detect coating degradation in accordance with the present inventive concept.

FIG. 10 is a method of analyzing the amplitude of the harmonic signal to detect coating degradation. It is a method of distinguishing coating degradation components from liftoff signal components by scaling the harmonic value to the fundamental value. This method accounts for variations in the fundamental frequency amplitude (also called the excitation frequency) that affect the amplitude of the measured harmonic signal. Using the components of the harmonic signal with coating degradation and probe liftoff signal components 1001 and the fundamental signal components 1002, the harmonic signal is scaled to the fundamental signal for each area of interest 1003 with the resulting signal having substantially all the liftoff signal components removed and substantially all the coating degradation signal components retained. This method may be accomplished by using the fundamental frequency where liftoff has occurred to scale the harmonic signal so as to correct for liftoff changes. If the fundamental frequency is reduced in amplitude, the amplitude of the resulting harmonic signal in that same position is correspondingly reduced. The result is a scaled signal having most of the liftoff signal components removed and the coating degradation components retained. Other methods of signal scaling may be used to distinguish liftoff signal components from coating degradation signal components.

Figure 11:
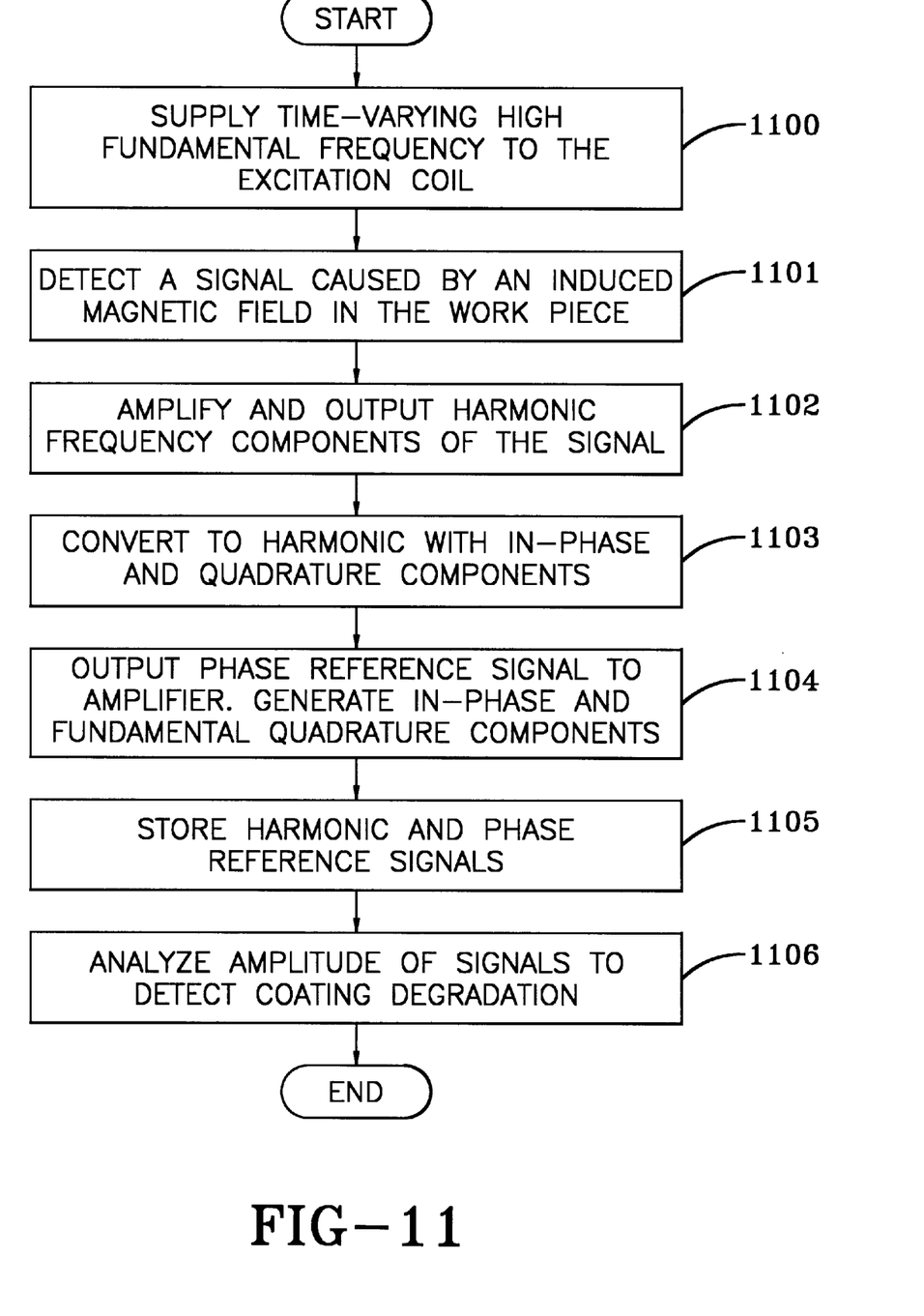
FIG. 11 is a flowchart of a method of using a high fundamental frequency to detect coating degradation in accordance with the present inventive concept.

FIG. 11 is a flowchart of a method of using a high fundamental frequency to detect coating degradation. The magnetic field produced by the nonlinear harmonics probe penetrates to different depths at different frequencies. Because penetration depth of the coating is inversely proportional to the square root of the frequency and is calculated using a known skin depth equation, high frequencies can be chosen to limit the skin penetration depth from near the surface of the coating through the entire coating thickness. A time varying current is supplied at a high fundamental frequency to an excitation coil 1100, positioned in close proximity to a surface of a workpiece having a metallic coating. If a voltage at harmonic frequencies signal is induced in a sensing coil 1101, it is amplified and its harmonic frequency components are output 1102 and converted to a harmonic signal with an in-phase signal component and a quadrature signal component 1103. A phase reference signal component is output to an amplifier which generates in-phase and quadrature fundamental signal components 1104. The harmonic signal and phase reference signal are stored 1105 and the harmonic signal amplitude is analyzed to detect coating degradation 1106. In one method of use, a single high fundamental frequency may be used (step 1100) which may correspond to a skin penetration depth that is less than the smallest thickness of the coating, so a coating thickness change in the coating outside of the smallest coating thickness does not affect the harmonic frequency components. By selecting the high fundamental frequency to be used, the depth of the sensing can be changed and sensitivity to variations in the thickness of the coating can be eliminated.

Alternatively, by performing nonlinear harmonics measurements at a number of selected high fundamental frequencies and comparing the amplitudes of the harmonic signals at those selected frequencies, coating degradation as a function of depth may be profiled. Therefore, in this embodiment, steps 1100 to 1105 may be repeated for a selected number of high fundamental frequencies, with the frequencies ranging between a frequency with a skin penetration depth that is near the surface of the coating to a frequency with a skin penetration depth equal to or greater than the entire coating thickness. If multiple high frequencies are used, the amplitudes of the resulting harmonic signals 1106 of each selected frequency can then be compared and used to profile coating degradation as a function of depth.

Another way of analyzing the data is to determine coating degradation while ignoring other interfering signals from other parameters such as those from liftoff and coating thickness. This may be done by performing a calibration where the coating degradation signals are measured for different degrees of degradation and the interfering signals are also measured. A least squares fit is then made to the data at different frequencies, but is fit only to the coating degradation response without regard to the interfering signals. This same approach can be taken using the fundamental as one of the frequencies. The equation is typically a polynomial of a given degree. An example of a second degree fit using two frequencies is:

$$D = C_1 + C_2 R_1 + C_3 R_1^2 + C_4 X_1 + C_5 X_1^2 + C_6 R_2 + C_7 R_2^2 + C_8 X_2 + C_9 X_2^2$$

where D is the amount of coating degradation, R1 and R2 are the in-phase components and X1 and X2 are the quadrature components, respectively of the two frequencies and C1 through C9 are weighting constants for the least squares fit.

What is claimed is:

1. A system for nondestructive testing utilizing nonlinear harmonics techniques to determine degradation within metallic protective coatings affixed to a surface of a workpiece comprising:
    a. means for supplying a time varying current at a fundamental frequency to a nonlinear harmonic sensor and for outputting a phase reference signal;
    b. the nonlinear harmonic sensor comprising:
        i. an excitation coil, positioned in close proximity to a surface of a workpiece having a metallic coating, for generating a magnetic field when supplied with the time varying current;
        ii. a sensing coil, positioned in close proximity to the surface of the workpiece, for detecting a signal caused by an induced magnetic field in the metallic coating;
    c. means for amplifying and selecting a portion of the detected signal that represents a harmonic frequency component of the signal and generating an output signal using the phase reference signal; and
    d. means for displaying the output signal.

2. A system according to claim 1, wherein when no harmonic signal caused by the induced magnetic field in the metallic coating is detected, the metallic protective coating is not degraded.

3. A system according to claim 1, wherein when the harmonic signal caused by the induced magnetic field in the metallic coating is detected, the metallic protective coating is degraded.

4. A system according to claim 1, wherein the means for displaying the output signal is a computer controlled display device.

5. A system according to claim 1, wherein the means for displaying the output signal is a meter that displays a harmonic amplitude of the output signal.

6. A system for nondestructive testing utilizing nonlinear harmonics techniques to determine degradation within metallic protective coatings comprising:
    a. means for supplying a time varying current at a fundamental frequency to a nonlinear harmonic sensor and for outputting a phase reference signal;
    b. the nonlinear harmonic sensor comprising:
        i. an excitation coil, positioned in close proximity to a surface of a workpiece having a metallic coating, for generating a magnetic field when supplied with the time varying current;
        ii. a sensing coil, positioned in close proximity to the surface of the workpiece, for detecting a signal caused by an induced magnetic field in the metallic coating;
    c. means for amplifying and selecting a portion of the detected signal that represents a harmonic frequency component of the signal and outputting a harmonic signal using the phase reference signal;
    d. means for storing the harmonic signal; and
    e. computer means for displaying and analyzing the harmonic signal to detect coating degradation.

7. A system according to claim 6, wherein when no harmonic signal caused by the induced magnetic field in the metallic coating is detected, the metallic coating is not degraded.

8. A system according to claim 6, wherein when the harmonic signal caused by the induced magnetic field in the metallic coating is detected, the metallic coating is degraded.

9. A system according to claim 6, wherein the harmonic signal is at a third harmonic frequency of the fundamental frequency.

10. A system according to claim 6, wherein the means for supplying the time varying current at the fundamental frequency to a nonlinear harmonic sensor and for outputting the phase reference signal is a signal generator and power amplifier.

11. A system according to claim 6, wherein:
    a. the harmonic signal stored for analysis comprises an in-phase signal component an a quadrature signal component; and
    b. the phase reference signal component is output to an amplifier which generates and in-phase and quadrature reference signal component.

12. A system according to claim 6, wherein the fundamental frequency is a selected frequency in the range of between about 1 kHz to about 10 MHz.

13. A system according to claim 6, wherein the means for amplifying and selecting the portion of the signal that represents the harmonic frequency component of the signal and generating a harmonic signal using the phase reference signal further comprises:
    a. filter means for filtering the output signal to remove frequencies other than harmonic frequencies; and
    b. means for frequency multiplying the phase reference signal and passing the multiplied phase reference signal to a lock-in amplifier that uses the multiplied phase reference signal and filtered harmonic signal to generate a complex harmonic signal with in-phase and quadrature signal components.

14. A system according to claim 6, wherein the nonlinear harmonic sensor comprises a plurality of nonlinear harmonics sensing devices positioned in close proximity to the surface of the workpiece to form sensor arrays.

15. A system according to claim 6, wherein the metallic coating is a high temperature protective coating.

16. A system according to claim 6, wherein the metallic coating contains elements selected from the group consisting of cobalt, nickel, chromium, yttrium and aluminum.

17. A system for nondestructive testing utilizing nonlinear harmonics techniques to determine degradation within metallic protective coatings affixed to a workpiece comprising:
   a. means, positioned in close proximity to a surface of a workpiece having a metallic coating, for generating a time varying magnetic field and outputting a phase reference signal;
   b. means for sensing, positioned in close proximity to the surface of the workpiece, a signal caused by an induced magnetic field in the metallic coating;
   c. means for amplifying the detected signal and detecting a harmonic frequency component of the signal;
   d. means for storing the harmonic frequency component; and
   e. computer means for analyzing an amplitude of the harmonic frequency component to detect coating degradation.

18. A method for nondestructive testing utilizing nonlinear harmonics techniques to determine degradation within metallic protective coatings affixed to a workpiece comprising the steps of:
   a. supplying a time varying current at a fundamental frequency to an excitation coil, positioned in close proximity to a surface of a workpiece having a metallic coating, for generating a magnetic field and outputting a fundamental phase reference signal;
   b. detecting any signal caused by an induced magnetic field using a sensing coil positioned in close proximity to the surface of the workpiece;
   c. if a signal is detected, amplifying and selecting a portion of the signal of step b that represents a harmonic frequency component of the signal and outputting a harmonic signal;
   d. storing the harmonic signal and phase reference signal; and
   e. analyzing the amplitude of the harmonic signal to detect coating degradation using a computer program.

19. A method for nondestructive testing utilizing nonlinear harmonics techniques to determine degradation within metallic protective coatings affixed to a workpiece comprising the steps of:
   a. supplying a time varying current at a fundamental frequency to an excitation coil, positioned in close proximity to a surface of a workpiece having a metallic coating, for generating a magnetic field and outputting a fundamental phase reference signal;
   b. detecting any signal caused by an induced magnetic field using a sensing coil positioned in close proximity to the surface of a workpiece;
   c. if the signal is detected, amplifying and selecting a portion of the detected signal of step b that represents a harmonic frequency component of the signal and outputting a harmonic signal;
   d. outputting the phase reference signal to an amplifier which generates an in-phase and quadrature fundamental signal component;
   e. storing the harmonic signal and the phase reference signal with the harmonic signal stored comprising an in-phase signal component and a quadrature signal component; and
   f. analyzing the amplitude of the harmonic signal to detect coating degradation using a computer program.

20. A method according to claim 19, in the amplifying and selecting step, further comprising the steps of:
   a. filtering the output signal to remove frequencies other than harmonic frequencies; and
   b. frequency multiplying the phase reference signal and passing the multiplied phase reference signal to a lock-in amplifier that uses the multiplied phase reference signal and filtered harmonic signal to generate a complex harmonic signal with in-phase and quadrature signal components.

21. A method according to claim 20, wherein the nonlinear harmonic sensor comprises a plurality of nonlinear harmonics sensing devices positioned in close proximity to the surface of the workpiece to form sensor arrays.

22. A method according to claim 19, wherein the harmonic signal is at a third harmonic frequency of the fundamental frequency.

23. A method according to claim 19, wherein the analyzing the amplitude of the harmonic signal to detect coating degradation using a computer program step, further comprises the steps of:
   a. analyzing the amplitude of the in-phase and quadrature harmonic signal components which contain coating degradation components and probe liftoff signal components;
   b. determining the amount to phase shift the in-phase and quadrature harmonic signal components to remove the liftoff signal components; and
   c. phase shifting the in-phase and quadrature signal components by a selected number of degrees to remove the liftoff signal components, with the resulting signal indicating the coating degradation components.

24. A method according to claim 19, wherein the analyzing the amplitude of the harmonic signal to detect coating degradation using a computer program step, further comprises the steps of:
   a. determining the amount to phase shift the in-phase and quadrature harmonic signal components to remove the liftoff signal components;
   b. phase shifting the in-phase and quadrature signal components by a selected number of degrees to remove the liftoff signal components;
   c. comparing the amplitude of the in-phase and quadrature harmonic signal components to an amplitude of a threshold signal level; and
   d. characterizing the amount of coating degradation using a calibration curve if the amplitude of the in-phase or quadrature harmonic signal is greater than the amplitude of the threshold level signal.

25. A method according to claim 24, further comprising determining the threshold level signal comprising:
   a. using a specimen that is the same material as the workpiece having the same coating on the surface of the workpiece;

b. placing a nonlinear harmonics sensing device on the specimen;

c. supplying a time varying current at a given frequency to the nonlinear harmonics sensing device and outputting a fundamental phase reference signal;

d. detecting a signal caused by induced magnetic field in the specimen;

e. amplifying and selecting a portion of the signal of step d that represents a harmonic frequency component of the signal and outputting a harmonic signal;

f. degrading the coating of the specimen by a known amount and repeating steps a through f for a fixed number of coating degradations;

g. constructing the calibration curve by plotting the harmonic signal corresponding to each degradation of the coating; and h. constructing the threshold signal level.

26. A method according to claim 24, further comprising determining the threshold level signal comprising:

a. using a specimen that is the same material as the workpiece and having the same coating applied to the workpiece with a known amount of degradation to the coating;

b. placing a nonlinear harmonics sensing device on the specimen;

c. supplying a time varying current at a given frequency to the nonlinear harmonics sensing device and outputting a fundamental phase reference signal;

d. detecting a signal caused by any induced magnetic field in the specimen;

e. amplifying and selecting a portion of the signal of step d that represents a harmonic frequency component of the signal and outputting a harmonic signal;

f. constructing the calibration curve by plotting the harmonic signal corresponding to the degradation of the coating; and g. constructing the threshold signal level.

27. A method according to claim 24, wherein the number of degrees of phase shifting is determined by using an optimization software program which phase shifts the signal in incremental amounts to determine a largest amplitude for a signal of interest and a smallest amplitude for a signal not of interest.

28. A method according to claim 19, wherein the analyzing the amplitude of the harmonic signal to detect coating degradation using a computer program step, further comprises the steps of:

a. using the amplitude of the harmonic signal components which contain coating degradation components and probe liftoff signal components;

b. using the amplitude of the fundamental signal components; and c. scaling the harmonic signal to the fundamental signal, the resulting signal having substantially all the liftoff signal components removed and substantially all the coating degradation components retained such that amount of coating degradation is indicated by changes in amplitude of the resulting signal.

29. A method for nondestructive testing utilizing nonlinear harmonics techniques to determine degradation within metallic protective coatings affixed to a workpiece comprising the steps of:

a. supplying a time varying current at a high fundamental frequency to an excitation coil, positioned in close proximity to a surface of a workpiece having a metallic coating, for generating a magnetic field and outputting a fundamental phase reference signal;

b. detecting any signal caused by an induced magnetic field using a sensing coil positioned in close proximity to the surface of a workpiece;

c. if the signal is detected, amplifying and selecting a portion of the signal of step b that represents harmonic frequency components of the signal and outputting an output signal;

d. converting the output signal containing the harmonic frequency components to a harmonic signal which comprises an in-phase signal component and a quadrature signal component;

e. outputting the phase reference signal component to an amplifier which generates and in-phase and quadrature fundamental signal component;

f. storing the harmonic signal and phase reference signal; and g. analyzing the harmonic signal amplitude to detect coating degradation.

30. A method according to claim 29, wherein the high fundamental frequency corresponds to a skin penetration depth that is less than or equal to a smallest coating thickness, so a coating thickness change in the coating outside of the smallest coating thickness does not affect the harmonic frequency components.

31. A method according to claim 29, further comprising:

a. repeating the method of claim 29, steps a through f, for a plurality of selected high fundamental frequencies, the selected frequencies ranging from between a frequency with a skin penetration depth that is near the surface of the coating to between a frequency with a skin penetration depth equal to or greater than the entire coating thickness; and b. comparing the amplitudes of the harmonic signals of each selected frequency to profile coating degradation as a function of depth.

* * * * *